United States Patent [19]

Cardin et al.

[11] Patent Number: 5,292,504
[45] Date of Patent: Mar. 8, 1994

[54] ANTI-LICE TREATMENT COMPOSITIONS

[75] Inventors: Caroline W. Cardin; David W. Peter, both of Cincinnati, Ohio

[73] Assignee: The Procter & Gamble Company, Cincinnati, Ohio

[21] Appl. No.: 841,232

[22] Filed: Feb. 21, 1992

Related U.S. Application Data

[63] Continuation of Ser. No. 510,659, Apr. 18, 1990, abandoned.

[51] Int. Cl.$^5$ .............................. A61K 7/075
[52] U.S. Cl. ...................... 424/70; 252/DIG. 13; 424/74; 424/405; 514/65; 514/72; 514/531; 514/881
[58] Field of Search ............ 424/405, 70, 74; 252/DIG. 13; 514/881, 65, 72, 531

[56] References Cited

U.S. PATENT DOCUMENTS

| | | | |
|---|---|---|---|
| 1,797,877 | 3/1931 | Moore | 564/291 |
| 3,155,591 | 11/1964 | Hilfer | 167/87 |
| 4,179,504 | 12/1979 | Lynch et al. | 424/248.4 |
| 4,183,913 | 1/1980 | Enders et al. | 424/45 |
| 4,238,499 | 12/1980 | Lover et al. | 424/273 |
| 4,269,824 | 5/1981 | Villamarin et al. | 424/70 |
| 4,518,593 | 5/1985 | Juvin et al. | 424/195.1 |
| 4,559,227 | 12/1985 | Chandra et al. | 424/70 |
| 4,668,666 | 5/1987 | Allan et al. | 514/63 |
| 4,822,614 | 4/1989 | Rodero | 424/405 |
| 4,835,148 | 5/1989 | Barford et al. | 514/179 |
| 4,885,107 | 12/1989 | Wetzel | 252/106 |
| 4,940,729 | 7/1990 | Matthewson | 514/521 |
| 4,948,576 | 8/1990 | Verdicchio et al. | 424/59 |
| 5,104,645 | 4/1992 | Cardin et al. | 424/70 |

FOREIGN PATENT DOCUMENTS

| | | | |
|---|---|---|---|
| 191236 | 8/1986 | European Pat. Off. | A01N 43/42 |
| 262885 | 4/1988 | European Pat. Off. | A61K 7/06 |
| 0285389 | 10/1988 | European Pat. Off. | |
| 2704066 | 8/1978 | Fed. Rep. of Germany | |
| 1538768 | 1/1979 | United Kingdom | A61K 7/06 |
| 2001852 | 2/1979 | United Kingdom | |
| 1593601 | 7/1981 | United Kingdom | A01N 25/00 |
| 1604857 | 12/1981 | United Kingdom | A61K 31/045 |

OTHER PUBLICATIONS

The Merck Index, 10th Edition, 1983; p. 1149; 7865.
Worthing, C. R. *The Pesticide Manual* 1987, The British Crop Protection Council, Thornton Heath, GB, Eight Edition, p. 726, paragraph 2.
Technical Data Refrence, Kelco Division of Merck & Co., Inc. "Structure of Xantham Gum".
CTFA Cosmetic Ingredient Dictionary, 3rd Ed. 1982, p. 42.
Clements, "The Actions of Pyrethroids Upon the Peripheral Nervous System and Associated Organs in the Locust", 8 *Pestic. Sci.* 661 (1977) U.S. Ser. No. 510,659, Cardin et al., filed Apr. 18, 1990.

*Primary Examiner*—Thurman K. Page
*Assistant Examiner*—Robert H. Harrison
*Attorney, Agent, or Firm*—John M. Howell; Michael E. Hilton; Leonard W. Lewis

[57] ABSTRACT

Ovicidal/pediculicidal anti-lice compositions comprising a mixture of actives wherein the ratio of synthetic pyrethroids to natural pyrethrins is from about 6:1 to about 10:1. Said active mixtures are incorporated into hair treatment compositions, such as shampoos, lotions and conditioners, which are stable at high storage temperatures, effective, safe and easy to use.

18 Claims, No Drawings

ANTI-LICE TREATMENT COMPOSITIONS

This is a continuation of application Ser. No. 07/510,659, filed on Apr. 18, 1990, now abandoned.

FIELD OF THE INVENTION

The invention relates to treatment compositions utilizing a combination of anti-lice active ingredients effective in killing adult human head lice and their eggs. Such compositions are used to make stable, safe, and simple to use hair treatment compositions, such as lotions, shampoos and conditioners.

BACKGROUND OF THE INVENTION

Infestation of the body by lice is an age old problem. Reference to these pests can be found throughout documented history. Lice have been responsible for the spread of typhus, causing decimation of many armies and navies of the military powers of the 15th, 16th, 17th and 18th centuries. Lice are still considered as disease vectors and present serious health problems throughout the world. Not only do lice carry a wide variety of bacteria on their exterior surfaces, but their fecal matter transmits disease when it enters the puncture wounds lice inflict during feeding.

The human lice genus includes pubic lice, body lice, and head lice. Although related, each of them have specific characteristics with regard to habitat and feeding. The present invention is most useful in treatment of head lice. Head lice are small hard-shelled ectoparasites which cling to hair follicles while feeding, mating and laying eggs. The louse must remain on the head as it will die within a short period of time when removed. Head lice proliferate at an incredible rate. A louse is ready to mate and reproduce within 10 hours after hatching. Under ideal conditions, a female louse may produce up to 300 eggs in its lifetime. Ideal conditions include an adequate food supply, environmental temperatures from about 28° C. to about 32° C., and relative humidity from about 70% to about 90%. Poor hygienic and grooming habits are also known to contribute significantly to the spread of lice. Thus, lice infestations are most serious in tropical areas where the inhabitants have both substandard hygienic facilities and practices.

The louse's hard keratinous shell serves as protection from external elements. Lice eggs (or ova) are similarly protected by a chitinous sheath surrounding the eggs and attached to the hair follicles. Although the lice may be affected by the use of an insecticide, often the eggs remain resistant to attack. Thus, the optimum chemical treatment should include both a pediculicide, which kills the adult lice, and an ovicide, which interrupts the gestation of the eggs.

Biologically active agents for the control of lice are well known in the art. Lindane (gamma-benzene hexachloride), synergized natural pyrethrins, and synthetic derived compounds known as pyrethroids have all been used as pediculicides in lice treatment compositions. However, since lindane has a poor safety profile and lice have developed a significant degree of resistance to it, natural pyrethrins and synthetic pyrethroids are now routinely chosen for use in pediculicide and ovicide compositions.

Natural pyrethrins are made from extracts of naturally insecticidal chrysanthemum flowers and have been used since the early 1930's. European Patent Application 191,236 published Aug. 20, 1986; European Patent Application 262,885, published Apr. 6, 1988; and British Patent Specification 1,593,601, published Jul. 22, 1981, all disclose the use of natural pyrethrins for treating lice. U.S. Pat. No. 4,668,666, Allan, issued May 26, 1987, notes that natural pyrethrin necessitates frequent follow-up treatments because its poor environmental stability only provides short term residual action.

Synthetic pyrethroids became popular during World War II when chrysanthemum flowers became nearly impossible to get. Besides being available at lower prices, they were also somewhat more stable than the natural product.

The toxicity of both natural and synthetic pediculicides upon insects is described in Clements, May, and Pesti, *The Actions of Pyrethroids upon the Peripheral Nervous System and Associated Organs in the Locust,* 8 Pesticide Science 661–680 (1977).

Although generally more effective against lice than natural pediculicides, some of the synthetic actives are more toxic to the subject being treated. To reduce safety risks to the user antilice compositions are formulated with a combination of natural and synthetic pediculicides. The combination is thought to be the most effective since natural pyrethrins are known to affect certain nerve response mechanisms that synthetic pyrethroids cannot. U.S. Pat. No. 4,668,666, Allan, discloses anti-lice treatment compositions containing combinations of natural pyrethrins and synthetic pyrethroids from about 5:1 to about 1:5. These compositions, however, are relatively unstable and the actives must be encapsulated with aryl siloxane polymers to minimize destabilization by environmental elements. Thus, aryl siloxane polymers are an essential component in the Allan compositions in order to achieve some degree of compositional stability. However, even the use of siloxanes alone does not prevent the separation of the actives in hair treatment compositions such as shampoos, lotions and conditioners at temperatures over 38° C. This is a particular problem in tropical areas where lice infestation is most prevalent. Once the actives separate, they cannot be reincorporated back into the lotion, shampoo or conditioner, thereby, negatively affecting the compositions, safety and effectiveness.

SUMMARY OF THE INVENTION

The present invention utilizes combinations of natural and synthetic pediculicides within specific ratios to form an efficacious and stable treatment against head lice. The combination of actives covers the full range of neurological responses absent in either active alone. This expansion of neurological control allows the use of lower doses of pediculicidal and ovicidal actives, improving the safety of the treatment. Furthermore, the actives do not separate out of the hair treatment compositions they are incorporated into, particularly at the higher storage temperature typically found in tropical areas where lice infestation is most prevalent. The superior stability of the hair treatment compositions discussed herein, improves the effectiveness and safety of said compositions.

Specifically, the present invention relates to pediculicidal/ovicidal compositions comprising (a) a synthetic pyrethroid; and (b) a natural pyrethrin; wherein the ratio of (a) to (b) is from about 6:1 to about 10:1. Hair care compositions such as shampoos, lotions and conditioners, containing these pediculicidal/ovicidal actives, as well as the method of their use for controlling head lice, are claimed.

All ratios, percentages, and parts given herein are "by weight" unless otherwise specified.

DETAILED DESCRIPTION OF THE INVENTION

The present invention relates to the combination of actives developed for controlling the infestation of the hair by human head lice. The combinations of actives claimed herein are incorporated into stable and safe hair care compositions such as lotions, shampoos, and conditioners. Such compositions contain the elements as described in the following paragraphs.

Anti-Lice Actives

The actives disclosed in the present invention comprise a mixture of synthetic pyrethroids and natural pyrethrins. In these mixtures, the ratio of pyrethroid to pyrethrin is from about 6:1 to about 10:1, preferably from about 7:1 to about 9:1; most preferably about 9:1. At these ratios, the hair treatment compositions remain stable particularly at the high storage temperatures.

Natural pyrethrins, which are derived from chrysanthemum flower heads, are the esters formed by the combination of cyclopentenolone alcohols (pyrethrolone, cinerolone and jasmolone) with chrysanthemic acid or pyrethric acid. Although there are many possible isomers, the natural pyrethrins are invariably dextrorotatory isomers of the trans form of the carboxylic acids. The natural pyrethrin active consists essentially of six different esters: Cinerin I, Cinerin 11, Pyrethrin I, Pyrethrin I, Jasmolin I and Jasmolin II. Pyrethrin I and Pyrethrin II comprise about 70% of the esters found in said active. Their chemical structures are:

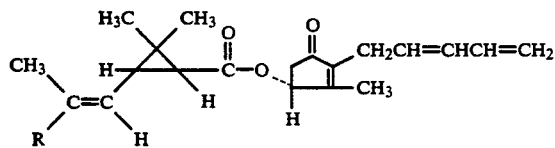

wherein Pyrethin I has R=CH₃ and Pyrethrin 11 has R=COOCH₃.

The synthetic analogues of the natural pyrethrins are herein called synthetic pyrethroids. These synthesized organic compounds are made by combining phenylacetic acid esters and esters of the dichlorovinyl analogues of chrysanthemic acid. Preferred synthetic pyrethroids include Phenothrin, Permethrin and mixtures thereof. These compounds have the basic chemical structure:

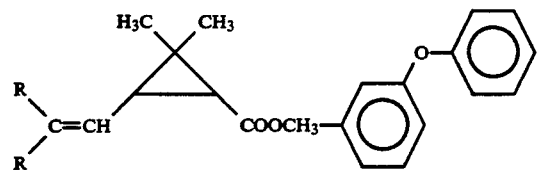

wherein Phenothrin has R=CH₃ and Permethrin has R=Cl.

The present inventions utilizes a combination of natural and synthetic pyrethrins for use on human head lice which provides a greater range of the neurological blocks. This broader range of control over the pest's neurogical responses lowers the threshold dose required to render the lice either paralyzed or dead. Furthermore, the stability of the hair care compositions described herein, particularly at high storage temperatures, is enhanced.

Optionally, piperonyl butoxide may be included with the mixed actives at levels from about 1% to about 5%. Piperonyl butoxide is a known additive included with the actives to inhibit development of resistance to actives by lice.

Compositions for Treating Head Lice

Anti-lice hair treatment compositions which may be formulated using the anti-lice mixtures disclosed herein include lotions, shampoos, and conditioners, among others.

1. Shampoos

Human hair becomes soiled due to its contact with the surrounding atmosphere and the build up of sebum secreted by the head. This causes the hair to have a dirty feel and an unattractive appearance, necessitating shampooing with frequent regularity. Shampooing with compositions disclosed herein not only cleans the hair, but also effectively treats for lice infestation.

Shampoo compositions of the present invention include the following components.

Anti-lice Actives

As disclosed supra, the shampoo compositions disclosed herein contain anti-lice actives which are mixtures of synthetic pyrethroids and natural pyrethrins in a ratio of from about 6:1 to about 10:1, preferably about 7:1 to about 9:1, most preferably about 9:1 at levels from about 0.10% to about 2.5%, preferably about 0.25% to about 1.5%, most preferably about 0.5% to about 1%.

Surfactant

The surfactant used herein is selected from any of a wide variety of synthetic anionic, amphoteric, zwitterionic and non-ionic surfactants. It is present in the shampoo composition at a level of from about 5% to about 30%, preferably from about 15% to about 25%.

Synthetic anionic surfactants can be exemplified by the alkali metal salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium, potassium or triethanolamine aklyl sulfates, especially those obtained by sulfating the higher alcohols ($C_8$–$C_{18}$ carbon atoms); sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms; sodium alkyl glyceryl ether sulfonates; the reaction product of fatty acids having from 10 to 22 carbon atoms esterified with isethionic acid and neutralized with sodium hydroxide; and water soluble salts of condensation products of fatty acids with sarcosine.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

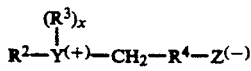

wherein $R^2$ contains an alkyl, alkenyl, or hydroxyalkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms, and Z is a radical selected from the group consisting of carboxylate, sulfonate, sulfate, phosphonate, and phosphate groups.

Examples include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphate;

3-(N,N-dimethyl-N-hexadecylammonio)propane-1-sulfonate;

3-(N,N-dimethyl-N-hexadecylammonio)-2-hydroxypropane-1-sulfonate;

N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxypentane-1-sulfate.

Other zwitterionic surfactants, such as betaines, are also useful in the present invention. Examples of betaines useful herein include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl) alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine, and the like; amido betaines and amidosulfobetaines, wherein a $RCONH(CH_2)_3$ radical is attached to the nitrogen atom of the betaine are also useful in this invention. The amido betaines are preferred for use in some of the compositions of this invention.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. 2,658,072, N-higher alkyl aspartic acids such as those produced according to the teaching of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base comprising the reaction product of ethylene diamine and excess propylene oxide, said base having a molecular weight on the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

wherein $R_1$ contains an alkyl, alkenyl, or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

wherein R contains an alkyl, alkenyl or monohydroxyalkyl radical of from about 8 to 18 carbon atoms, from 0 to about 10 ethylene oxide moieties and from 0 to 1 glyceryl moiety, and R' and R" are each alkyl or monohydroxyalkyl groups containing from 1 to about 3 carbon atoms. The arrow in the formula is a conventional representation of a semipolar bond. Examples of suitable phosphine oxides include: dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxyalkyl radical of 1 to about 3 atoms (usually methyl) and one long hydrophobic chain which contain alkyl, alkenyl, hydroxyalkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Many additional nonsoap surfactants are described in *McCutcheon's Detergents and Emulsifiers*, 1983 Annual, published by Allured Publishing Corporation; incorporated herein by reference.

The above-mentioned surfactants can be used alone or in combination in the shampoo compositions of the present invention. Anionic surfactants, particularly the alkyl sulfates, the ethoxylated alkyl sulfates and mixtures thereof, as well as the amido betaines, are preferred for use herein.

Amide

Amides enhance the lathering of the composition by emulsifying the shampoo components and the anti-lice actives. The amides used in the present compositions can be any of the alkanolamides of fatty acids known for use in shampoos. These are generally mono- and diethanolamides of fatty acids having from about 8 to about 14 carbon atoms. Other suitable amides are those having multiple ethoxy groups such as PEG-3 lauramide.

In the shampoo compositions disclosed herein, the amide is present at a level of about about 1% to about 7%, preferably from about 2% to about 5%, of the composition. Preferred are coconut monoethanolamide, coconut diethanolamide, and mixtures thereof.

Water

The shampoo compositions hereof also comprise water.

Water is typically present in the shampoo at a level of from about 50% to about 80%, preferably from about 60% to about 75%. After adding water, the relative viscosity of the present compositions is generally in the range of from about 4,000 centipoise (hereinafter cp) to about 25,000 cp, preferably from about 4,000 cp to about 12,000 cp, most preferably from about 4,000 cp to about 5,500 cp, measured at 1 RPM at 26.7° C. for 3 minutes using a Wells-Brookfield viscometer Model DV-CP-2 DVII, Model Cone CP-41. Viscosity modifiers and hydrotropes, listed below, may be included to bring the composition's viscosity within the range just mentioned.

Optional Components

Silicone compounds may be incorporated into the shampoo compositions to impart conditioning benefits to the hair and to facilitate removal of the dead lice and their eggs. Non-volatile silicone materials are used at levels from about 1% to about 10% of the compositions herein. Such silicone compounds are disclosed in U.S. Pat. No. 2,826,551, Geen, issued Mar. 11, 1958; U.S. Pat. No. 3,964,500, Drakoff, issued Jun. 22, 1976; U.S. Pat. No. 4,152,416, Spitzer, issued May 1, 1979; U.S. Pat. No. 4,221,688, Johnson et al., issued Sep. 9, 1980; U.S. Pat. No. 4,364,837, Pader, issued Dec. 21, 1982; U.S. Pat. No. 4,515,784, Bogardus et al., issued May 7, 1985; U.S. Pat. No. 4,704,272, Oh et al., issued Nov. 3, 1987; U.S. Pat. No. 4,728,457, Fieler et al., issued Mar. 1, 1988; U.S. Pat. No. 4,741,855, Grote et al., issued May 3, 1988; U.S. Pat. No. 4,764,363, Bolich, issued Aug. 16, 1988; U.S. Pat. No. 4,788,006, Bolich et al., issued Nov. 29, 1988; U.S. Pat. No. 4,834,968, Bolich, issued May 30,1989; and U.S. Pat. No. 4,842,850, Vu, issued Jun. 27, 1989; all incorporated herein by reference.

Non-volatile silicone-containing compounds are preferred herein and are used at levels of from about 0.1% to about 10%, preferably from about 0.25% to about 3%, by weight of the composition. Non-volatile silicones are selected from the group consisting of polyalkyl siloxanes, poly alkylaryl siloxanes, polyether siloxane copolymers and mixtures thereof.

Polyalkyl siloxanes useful herein include, for example, polydimethyl siloxanes (PDMS) with viscosities ranging from about 5 to 15,000,000 centipoise (cp) at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, Jul. 20, 1970.

Polyalkylaryl siloxanes that may be used include polymethylphenyl siloxanes having viscosities of from about 5 to about 15,000,000 cp at 25° C. These siloxanes are available, for example, from the General Electric Company as SF 1075 methyl phenyl fluid or from Dow Corning as 556 Cosmetic Grade Fluid.

Polyether siloxane copolymers that may be used include polypropylene oxide modified polydimethylsiloxanes. These are available, for example, from Dow Corning as DC-1248. Ethylene oxide or mixtures of ethylene oxide and propylene oxide may also be used. The water insoluble ones are preferred.

Generally, these silicone compounds, described above, condition the hair. The conditioning benefit is due to the ability of the siloxanes to lubricate the hair providing wet and dry combing benefits. Also, viscous, higher molecular weight siloxanes provide the best conditioning benefits and are therefore preferred for use in the present shampoo composition. It has been found the fluids and gums of the above described siloxane polymers are most desirable for use herein. These siloxane polymer gums are rigid as opposed to a liquid or fluid, with high mass molecular weights of from about 200,000 to about 1,000,000 as viscosities from about 100,000 cp to about 150,000,000 cp at 25° C. Such gums are discussed in detail in W. Noll, *Chemistry and Technology of Silicones*, New York academic Press, 1968; and General Electric, Silicones and Rubber Product Data Sheet SE30, SE33, SE54 and SE76; and Mark, Bikales, Overberger, Mengle, *Encyclopedia of Science and Engineering*, Vol. 15 (2df ed., 1989), all incorporated herein by reference.

Shampoo compositions disclosed herein may incorporate suspending agents to assist in maintaining long term stability. Suspending agents useful herein are selected form the group consisting of fatty amphiphilic crystalline materials having needle-like or platelet structures, polymeric materials, clays, fumed metal oxides, and mixtures thereof. These agents are, for example, disclosed in U.S. Pat. No. 4,704,272, Oh et al., issued Nov. 3, 1987; U.S. Pat. No. 4,728,457, Fieler et al., issued Mar. 1, 1988; and U.S. Pat. No. 4,741,855, Grote et al., issued May 3, 1988; all incorporated herein by reference.

Crystalline amphiphilic materials, suitable herein, are those which have needle or platelet-type structures. Such compounds include long chain ($C_{16}$–$C_{22}$) acyl derivatives, such as ethylene glycol esters of fatty acids (e.g., ethylene glycol disterate); long chain ($C_{16}$–$C_{22}$) alkanol amides of fatty acids, such as stearamide MEA, stearyl stearate, and distearyl dithiopropionate; and mixtures thereof.

Polymeric materials used as suspending agents are selected from the group consisting of cross-linked polyacylic acids such as the Carbopol series, available from the B. F. Goodrich Chemical Company, guar gum and its derivatives, xanthan gum, cross linked copolymers of ethylene/maleic anhydrides, and mixtures thereof.

Clays and fumed metal oxides are also effective suspending agents. Included herein are magnesium aluminum silicates, such as the Veegum series, available from R. T. Vanderbilt Company, Inc.; sodium aluminum silicates, such as the Laponite series, available from Laponite United States; fumed silica, fumed alumina, fumed titania and mixtures thereof.

In the present invention suspending agents are used at from about 0.5% to about 5%, preferably from 0.5% to about 3%. Preferred are the long chain acyl derivative such as ethylene glycol esters of fatty acids. Most preferred is ethylene glycol distearate.

The shampoo compositions herein can also contain a variety of other components suitable for rendering such compositions more cosmetically acceptable. Such optional ingredients are well known to those skilled in the art, e.g., preservatives, such as methyl paraben, propyl paraben, methylisothiazolinone and imidazolidinyl urea; thickeners and viscosity modifiers, such as amine oxides, block polymers of ethylene oxide and propylene oxide (such as Pluronic F88 offered by BASF Wyandotte), fatty alcohols (such as cetearyl alcohol), sodium chloride, ammonium chloride, sodium sulfate, polyvinyl alcohol, propylene glycol, and ethyl alcohol; hydrotropes, such as xylene sulfonate; pH adjusting agents, such as citric acid, succinic acid, phosphoric acid, sodium hydroxide, and sodium carbonate; perfumes; dyes; quaternary ammonium compounds, such as Polyquaternium 41; sequestering agents, such as disodium ethylenediamine tetraacetate; and pearlescing agents, such as distearic acid ester of ethylene glycol, stearic acid and palmitic acid diesters of polyethylene glycol, and stearic acid monoethanolamide. These optional components generally are used individually at a level of from about 0.1% to about 10% of the composition.

The shampoo compositions of the present invention are used in a conventional manner for cleaning hair. From about 10 g to about 30 g of a composition is applied to wet hair and worked through both hair and scalp. The composition is left on for approximately 6–10 minutes and then rinsed from the hair. This is repeated until hair is clean.

2. Conditioners

In general, products which improve the appearance, feel, and manageability of hair have gained increasing acceptance and popularity with consumers. The utility of such compositions is particularly important with the increased use of such hair treatments as permanent waving, dyeing, teasing, and bleaching. The physical condition of hair can also be affected by atmospheric conditions, such as sunlight, which may cause photo-catalyzed oxidation. These factors may result in hair with poor texture, which is difficult to manage and comb, whether wet or dry.

Compositions which "condition" hair generally improve the hair's manageability and appearance. Such conditioning products are well known and include "rinse-type" products, which are rinsed off shortly after being applied to clean hair, and "deep conditioners" which remain on the hair for extended periods of time. Conditioning the hair with compositions disclosed herein also effectively treats the lice infestation.

Anti-Lice Actives

As disclosed supra, the active mixtures containing synthetic pyrethroids and natural pyrethrins are formulated in hair conditioners. In addition to killing lice, these conditioners facilitate the removal of the dead lice and eggs during combing. The ratio of synthetic pyrethroids to natural pyrethrins is from about 6:1 to about 10:1, preferably about 7:1 to about 9:1, most preferably about 9:1 at levels from about 0.01% to about 2.5%, preferably about 0.5% to about 1.5%, most preferably about 1%.

Conditioning Actives

Conditioners comprising long chain quaternary ammonium compounds combined with lipid materials, such as fatty alcohols, are disclosed in U.S. Pat. No. 3,155,591, Hilfer, issued Nov. 3, 1964, and U.S. Pat. No. 4,269,824, Villamarin, et al., issued May 26, 1981, both incorporated herein by reference. Lipids and quaternary ammonium compounds are used to form gel-type conditioner compositions having good in-use cosmetic and rheological characteristics. Such gel-type compositions are generally described in the following documents, all incorporated herein by reference: Barry, "The Self Bodying Action of the Mixed Emulsifier Sodium Docecyl Sulfate/Cetyl Alcohol", 28 *J. of Colloid and Interface Science* 82-91 (1968); Barry et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689-708 (1971); and Barry et al., "Rheology of Systems Containing Cetomacrogo/1000 - (etostearyl alcohol), I. Self-Bodying Action", 38 *J. of Colloid and Interface Science,* 616-625 (1972).

The lipid materials used in the conditioner described herein are at a level of from about 0.5% to about 3%. These lipids are essentially water-insoluble, and contain hydrophobic and hydrophilic moieties. They include natural and synthetically-derived fatty materials selected from the group consisting of acids, acid derivatives, alcohols, esters, ethers, ketones, amides, and mixtures thereof having alkyl chain lengths from about 12 to about 22 carbon atoms; preferably from 16 to 18 carbon atoms in length. Fatty alcohols and fatty esters are preferred.

Fatty alcohols useful herein are disclosed in the following documents, all incorporated by reference herein: U.S. Pat. No. 3,155,591, Hilfer, issued Nov. 3, 1964; U.S. Pat. No. 4,165,369, Watanabe et al., issued May 26, 1981; British Patent Specification 1,532,585, published Nov. 15, 1978; Fukushima et al., "The Effect of Cetostearyl Alcohol in Cosmetic Emulsions", 98 *Cosmetics & Toiletries* 89-102 (1983); and Hunting, *Encyclopedia of Conditioning Rinse Ingredients,* at 204 (1987). Fatty alcohols are materials which contain a hydroxyl group attached to a fat chain. The fatty alcohols used herein are selected from the group consisting of $C_{12}$-$C_{16}$ alcohols, cetearyl alcohol, cetyl alcohol, isostearyl alcohol, lanolin alcohol, lauryl alcohol, oleyl alcohol, stearyl alcohol, and mixtures thereof. Preferred are cetyl alcohol, stearyl alcohol, and mixtures thereof. A particularly preferred fatty alcohol is comprised of a mixture of cetyl alcohol and stearyl alcohol containing from about 55% to about 65% (by weight of mixture) of cetyl alcohol.

Fatty esters useful herein are disclosed in U.S. Pat. No. 3,341,465, Kaufman, et al., issued Sep. 12, 1967 (incorporated by reference herein). Fatty esters are fatty acids whose active hydrogen has been replaced by the alkyl group of a monohydric alcohol. In the present invention the monohydric alcohols are fatty alcohols as described above. The fatty esters used herein are selected from the group consisting of cetyl lactate, cetyl octanoate, cetyl palmitate, cetyl stearate, glyceryl monostearate, glyceryl laurate, glyceryl myristate, glyceryl oleate, glyceryl stearate, glyceryl monoacetate, and mixtures thereof. Most preferred are cetyl palmitate, glycerol monostearate, and mixtures thereof.

The cationic surfactants, used herein either singly or in combination, are at a level of from about 0.1% to about 5% of the final composition. Said surfactants selected herein contain amino or quaternary ammonium hydrophilic moieties which are positively charged when dissolved in the aqueous composition of the present invention. Some of the cationic surfactants useful herein are disclosed in the following documents, all incorporated herein by reference: *McCutcheon's Detergents & Emulsifiers,* (North American edition, M. C. Publishing Co., 1979); Schwartz et al., *Surface Active Agents, Their Chemistry and Technology,* New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Quaternary ammonium cationic surfactant materials useful herein are those of the general formula:

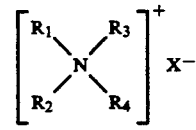

wherein $R_1$ is hydrogen, an aliphatic group of from 1 to 22 carbon atoms, or an aromatic, aryl or alkylaryl group having from 12 to 22 carbon atoms; $R_2$ is an aliphatic group having from 1 to 22 atoms; $R_3$ and $R_4$ are each alkyl groups having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amido groups.

Other quaternary ammonium salts useful herein are of the formula:

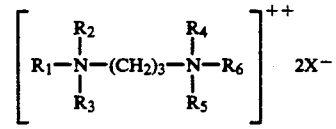

wherein at least one, but no more than 3 of the R groups is an aliphatic group having from 16 to 22 carbon atoms, and the remaining R groups are selected from hydrogen and alkyl groups having from 1 to 4 carbon atoms, and X is an ion selected from halogen, acetate, phosphate, nitrate and alkyl sulfate radicals. Such quaternary ammonium salts include tallow propane diammonium dichloride.

Quaternary ammonium salts useful herein include dialkyldimethylammonium chlorides, wherein in the alkyl groups have from 12 to 22 carbon atoms. These alkyl groups may be derived from long-chain fatty acids, such as hydrogenated tallow fatty acid. Tallow fatty acid gives rise to quaternary compounds wherein $R_1$ and $R_2$ predominantly have from 16 to 18 carbon atoms. Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Preferred quaternary ammonium salts useful herein include ditallow dimethyl ammonium chloride, dicetyl dimethyl ammonium chloride, stearyl dimethyl benzyl ammonium chloride, cetyl trimethyl ammonium chloride, tricetyl methyl ammonium chloride, and mixtures thereof. Di(hydrogenated tallow) dimethyl ammonium chloride or Quaternium-18, is a particularly preferred quaternary ammonium salt, and is available from the Sherex Chemical Company, Inc. as Adogen 442 and Adogen 442-100P.

Salts of primary, secondary and tertiary fatty amines are also usable as a cationic surfactants. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamine, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal et al., issued Jun. 23, 1981 (incorporated by reference herein.)

Water

Water is the last essential ingredient in the conditioner composition disclosed herein. Water is added in an amount in order to q.s. the mixture to 100%.

Optional Ingredients

Silicone conditioning agents are known in the art to have acceptable in-use, cosmetic, and rheological characteristics. Both silicone oils and silicone polymers are well known for this use. For example, British Patent Specification 1,598,567, Lewis et al., published Sep. 23, 1981, discloses hair conditioners containing volatile silicones and certain surfactants. British Patent Specification 999,222, published Jul. 21, 1965, discloses organosilicone polymers in water-alcohol mixtures for use as hair conditioners. U.S. Pat. No. 4,374,825, Bolich et al., issued Feb. 22, 1983, discloses conditioners containing hydrocarbon or silicone conditioning agents, certain nonionic water-soluble thickening agents, and a cationic conditioning agent. U.S. Pat. No. 4,387,090, Bolich, issued Jun. 7, 1983, discloses conditioning compositions containing volatile hydrocarbon or silicone conditioning agents and certain polymeric thickening agents. U.K. Patent Specification 2,066,659, Abe, published Jul. 15, 1981, discloses conditioning hair rinse compositions comprising quaternary ammonium salts, silicone materials, and propylene glycol.

The composition of the present invention may include one or more silicones disclosed for use in the shampoo compositions disclosed supra. These silicones include volatile and non-volatile polyalkyl siloxanes, polyalkylaryl siloxanes, and mixtures thereof. Said silicones may be used at levels from about 0.2% to about 5% of the final composition.

Volatile silicone fluids for use herein are disclosed in U.S. Pat. No. 4,842,850, Vu, issued Jun. 27, 1989. Preferred herein are the cyclic siloxanes having the structure:

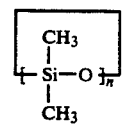

wherein n is from 3 to 7 with the siloxane having a viscosity of less than 10 cp at 25° C. Most preferred is cyclomethicone with n=5.

As with shampoos, the higher viscosity silicone gums of the siloxanes disclosed supra are preferred. Such gums are rigid as opposed to a fluid with high molecular weights of from about 200,000 to about 1,000,000 and viscosities from about 100,000 cp to about 150,000,000 cp at 25° C. Most preferred are the polydimethylsiloxane gums.

Despite the use of silicone gum and fluids, a significant amount of the lipid materials in the conditioner is also deposited on the hair, leaving it greasy. European Patent Application 155,806, published Sep. 25, 1985 (incorporated herein by reference), discloses conditioners comprising silicone copolyols together with silicone gums and silicone fluids to reduce the deposition of the lipid material on the hair. The conditioner composition of the present invention may incorporate such silicone copolyols to optimize the conditioning benefits of the anti-lice treatment disclosed herein.

The silicone copolyols are polyalkylene oxide modified dimethylpolysiloxanes, herein referred to as a "dimethicone copolyols", which act as an emulsifier and reduces the deposition of the vehicle materials (lipid materials and/or cationic surfactants) on the hair. The dimethicone copolyols include the polyalkylene oxide modified polydimethylsiloxanes of the following formulas:

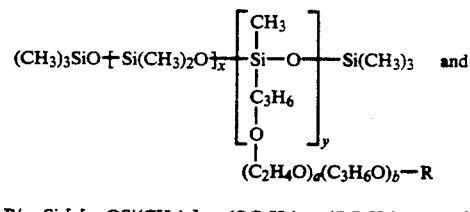

wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer of from 1 to 100, preferably from 20 to 30; y is an integer of 1 to 20, preferably from 2 to 10; and a and b are integers individually from 0 to 50, with a+b not less than 1; preferably a and b are from 20 to 30.

The silicone copolyol is present at a level of from about 0.1% to about 10%, preferably from about 0.1% to about 2%, of the final composition.

Dimethicone copolyols are preferred for use herein and are disclosed in the following patent documents, all incorporated herein by reference: European Patent Application 155,806, published Sep. 25, 1985; U.S. Pat. No. 4,122,029, Gee et al., issued Oct. 24, 1978; U.S. Pat. No. 4,265,878, Keil, issued May 5, 1981; U.S. Pat. No. 4,421,769, Dixon et al., issued Dec. 20, 1983; British Patent Specification 2,066,659, Abe, published Jul. 15, 1981, and Canadian Patent 727,588, Kuehns, issued Feb. 8, 1966. Commercially-available dimethicone copolyols useful herein include Silwet Surface Active Copolymers (manufactured by the Union Carbide Corporation); Dow Corning Silicone Surfactants (manufactured by the Dow Corning Corporation); Silicone Copolymer F-754 (manufactured by SWS Silicones Corp.); and Rhodorsil 70646 Fluid (manufactured by Rhone Poulenc, Inc.). Dow Corning 190 Silicone Surfactant is a preferred dimethicone copolyol.

The compositions of this invention may also contain components which modify the physical and performance characteristics of the conditioning product. Such components include additional surfactants, salts, buffers, thickeners, solvents, opacifiers, pearlescent aids, preservatives, fragrance, colorants, dyes, pigments, chelators, sunscreens, vitamins, and medicinal agents. Examples of such components are disclosed in U.S. Pat. No. 4,387,090, Bolich, Jr., issued Jun. 7, 1983, incorporated herein by reference.

The compositions of the present invention may contain optional surfactant materials, at levels such that the total level of surfactant present in the composition (including the cationic surfactant vehicle material, described above) is from about 0.05% to about 5%. These optional surfactant materials may be anionic, nonionic or amphoteric, such as ceteareth-20, steareth-20, sorbitan monoesters, sodium tallow alkylsulfate, and tallow betaine. Optional surfactant materials are described in the following documents, all incorporated by reference herein: *Detergents & Emulsifiers*, (M.C. Publishing Co., North American edition, 1979); Schwartz et al., *Surface Active Agents, Their Chemistry and Technology* (1949); andf U.S. Pat. No. 3,929,678, Laughlin et al., issued Dec. 30, 1975.

Preferred optional surfactant materials, useful herein, are nonionic. Such surfactants are most commonly produced by the condensation of an alkylene oxide (hydrophilic in nature) with an organic hydrophobic compound, which is usually aliphatic or alkyl aromatic in nature. The length of the hydrophilic or polyalkylene moiety which is condensed with any particular hydrophobic compound can be readily adjusted to yield a water-soluble compound having the desired degree of balance between hydrophilic and hydrophobic elements. Such nonionic surfactants include polyethylene oxide condensates of alkyl phenols, condensation products of aliphatic alcohols with ethylene oxide, condensation products of ethylene oxide with a hydrophobic base formed by condensation of propylene oxide with propylene glycol, and condensation products of ethylene oxide with the product resulting from the reaction of propylene oxide and ethylene diamine. Another variety of nonionic surfactant is the non-polar nonionic surfactants, typified by the amine oxide surfactants. Preferred nonionic surfactants include ceteareth-20, steareth-20 and ceteth-2.

Salts and buffers may also be added in order to modify the product rheology. For example, salts such as potassium chloride, ammonium chloride, and sodium chloride, may be added at levels of from about 0.001% to about 1%. Buffers, such as citrate or phosphate buffers, may also be used. Preferably the present compositions, as finally formulated, have a pH of from about 3 to about 10, most preferably from about 3 to about 7.

Additional conditioning components may also be incorporated into the compositions of the present invention. For example, proteins may be added at levels of from about 0.1% to about 10%. Cationic proteins may also serve as surfactant vehicle materials in the present invention.

Thickening agents are also preferred optional components useful in the present invention. Such thickeners include nonionic thickening agents, incorporated at levels of from about 0.1% to about 8%. Such agents are polymers which exhibit viscosities exceeding about 20,000 centipoise at low shear (about $10^{-2}$ sec$^{-1}$). Included among such polymers are polyoxyethylene, guar gum, methylcellulose, methyl hydroxypropyl cellulose, polypropyl cellulose, polypropyl hydroxyethyl cellulose, hydroxyethyl cellulose, starches and starch derivatives, and mixtures thereof. Nonionic thickening agents are disclosed in U.S. Pat. No. 4,387,090, Bolich et al., issued Jun. 7, 1983, incorporated by reference herein. Said thickening agents are used to bring to viscosity of the composition from about 10,625 cp to about 14,375 cp as measured with a Wells-Brookfield viscometer, Model RVT DV-CP-2, DV-11, Model Cone CP-52 using ½ ml at 1 rpm at 26.7° C. for 1 minute.

The hair conditioning compositions of the present invention are generally used on the hair after all shampoo has been rinsed off. The present invention provides methods of conditioning hair, comprising the steps of:

(a) applying from about 10 grams to about 30 grams of a composition of the present invention to wet hair;

(b) working said composition through the hair and scalp;

(c) leaving the composition on the hair and scalp for about 6-10 minutes; and (d) rinsing said composition from the hair.

3. Lotions

Anti-lice lotions are well known in the art. Such lotions can be applied directly onto the hair in liquid form or in spray form. They are formulated to be applied to the hair, but not immediately rinsed off.

Anti-lice Actives

Anti-lice actives used herein are those disclosed supra. The ratio of synthetic pyrethroids to natural pyrethrins is from about 6:1 to about 10:1, preferably about 7:1 to about 9:1, most preferably about 9:1 at levels from about 0.1% to about 2.5%, preferably about 0.25% to about 1.5%, most preferably about 0.5%.

Liquid Vehicle

In addition to the actives disclosed above, lotion compositions of the present invention utilize a liquid vehicle such as alcohol, water and mixtures thereof, to assist in delivery of the active to the hair. Alcohols are selected from the group consisting of monohydric alcohols such as methanol, ethanol, isopropanol and mixtures thereof. Since alcohols can have a deleterious effect upon the stability of the active compositions, water alone is most preferred as the vehicle. The vehicle is added in an amount necessary to q.s. the composition to 100%.

Optional Components

The lotion compositions of the present invention may include optional components to provide benefits to the hair in addition to the anti-lice activity. Lotion compositions of the present invention may include the following components: preservatives and antimicrobials, such as DMDM hydantoin and tetrasodium EDTA; pH balancing agents, such as sodium citrate and citric acid; emulsifiers, such as PEG-60 castor oil; and thickeners and viscosity modifiers, such as polyvinylpyrrolidone. Such components, when included, generally are used individually at a level from about 0.01% to about 10%.

Conditioning agent may be included to facilitate the removal of dead lice and eggs from the hair and to provide good wet and dry combing. Conditioning agents used herein are described in the conditioning compositions disclosed supra and include quaternary ammonium salts, fatty amines and mixtures thereof. Conditioning agents are used at levels from about 0.1% to about 1%, preferably from about 0.4% to about 0.6%. Preferred conditioning agents are quaternary ammonium salts.

Preferred quaternary ammonium salts include dialkyldimethylammonium chlorides, wherein in the alkyl groups have from 12 to 22 carbon atoms. These alkyl groups may be derived from long-chain fatty acids, such as hydrogenated tallow fatty acid. Tallow fatty acid gives rise to quaternary compounds wherein $R_1$ and $R_2$ predominantly have from 16 to 18 carbon atoms. Examples of quaternary ammonium salts useful in the lotion compositions include di(hydrogenated) tallow dimethyl ammonium chloride, dicetyl dimethyl ammonium chloride, tricetyl methyl ammonium chloride, cetyl trimethyl ammonium chloride, stearyl dimethyl benzyl ammonium chloride, and mixtures thereof. Most preferred is dicetyl dimethyl ammonium chloride.

Alcohol synergizers may also be added to the lotion compositions disclosed herein to enhance the anti-lice activity of the pediculicidal actives. The alcohols used in the lotion composition are selected from the group consisting of phenyl $C_2$–$C_6$ alkanols, phenyl $C_2$–$C_6$ diols, $C_2$–$C_8$ alkylene diols, and mixtures thereof. These synergizers may be included at levels from about 0.25% to about 10%, wherein the level of phenyl alkanols, phenyl diols, and mixtures thereof, does not exceed 5% of the composition. Preferably the level is about 0.5% to about 5% of the composition, most preferably from about 2% to about 4%. Preferred is hexylene glycol.

The lotion compositions of the present invention are generally applied in amounts from about 10 ml to about 50 ml directly to hair. The lotion is worked through the hair and left on for at least about 30 minutes. The hair is then generally cleansed with a shampoo composition before rinsing with water.

EXAMPLE I

A lotion composition of the present invention is as follows.

| Component | Weight (%) |
|---|---|
| Polyvinyl Pyrrolidone | 0.50 |
| DMDM Hydantoin | 0.20 |
| Tetrasodium EDTA | 0.13 |
| Citric Acid | 0.05 |
| PEG-60 Castor Oil | 0.50 |
| Hexylene Glycol | 4.00 |
| Dicetyl Dimethyl Ammonium Chloride | 0.38 |
| Natural Pyrethrins | 0.05 |
| Permethrin[1] | 0.45 |
| Water        q.s. to | 100.00 |

[1] Available from Mitchell Cotts Chemicals.

The composition is prepared by first mixing the natural pyrethrins and synthetic pyrethroid (permethrin) together in a beaker then adding it to a tank containing a mixture of PEG-60 castor oil, hexylene glycol, propylene glycol and dicetyl dimethyl ammonium chloride at between 35° C. to 38° C. In a second tank, mix polyvinyl pyrrolidone, DMDM hydantoin, tetrasodium EDTA and citric acid and bring to a temperature between 35° C. to 38° C. The contents of the first tank are added to the second tank and mixed until uniform. Cool the mixture to about 27° C., and empty into storage drums.

EXAMPLE II

A lotion composition of the present invention is as follows.

| Component | Weight (%) |
|---|---|
| Polyvinyl Pyrrolidone | 0.50 |
| DMDM Hydantoin | 0.20 |
| Tetrasodium EDTA | 0.13 |
| Citric Acid | 0.05 |
| PEG-60 Castor Oil | 0.50 |
| Hexylene Glycol | 2.00 |
| Propylene Glycol | 2.00 |
| Dicetyl Dimethyl Ammonium Chloride | 0.38 |
| Natural Pyrethrins | 0.025 |
| Permethrin[1] | 0.225 |
| Water        q.s. to | 100.00 |

[1] Available from ICI Agrochemicals.

The above composition is prepared by the same procedure as noted in Example I.

Example III

A lotion composition of the present invention is as follows.

| Component | Weight (%) |
|---|---|
| Polyvinyl Pyrrolidone | 0.50 |
| DMDM Hydantoin | 0.20 |
| Tetrasodium EDTA | 0.13 |
| Citric Acid | 0.05 |
| Isopropanol | 1.00 |
| PEG-60 Castor Oil | 0.50 |
| Hexylene Glycol | 4.00 |
| Dicetyl Dimethyl Ammonium Chloride | 0.60 |
| Natural Pyrethrins | 0.01 |
| Phenothrin[1] | 0.09 |
| Water        q.s. to | 100.00 |

[1] Available from Sumitomo Chemical Company as Sumithrin.

The above composition is prepared by the same procedure as noted in Example I.

All the above lotion compositions, when applied to the hair, and left on for at least ½ hour before being shampooed or rinsed out, are useful as anti-lice treatments.

EXAMPLE IV

A shampoo composition of the present invention is as follows

| Component | Weight % |
|---|---|
| Ammonium Laureth Sulfate | 10.40 |
| Ammonium Lauryl Sulfate | 9.50 |
| Coconut Monoethanolamide | 4.00 |
| Ethylene Glycol Distearate | 3.00 |
| DMDM Hydantoin | 0.20 |
| Monosodium phosphate | 0.10 |
| Disodium phosphate | 0.25 |
| Citric Acid | 0.07 |
| Ammonium Xylenesulfonate | 1.58 |
| Natural Pyrethrins | 0.05 |
| Permethrin[1] | 0.45 |

| Component | Weight % |
|---|---|
| Water q.s. to | 100.00 |

[1] Available from Fairfield American Company.

This composition is prepared by adding the ammonium lauryl sulfate to a tank and heating to between about 66° C. to about 69° C. While maintaining this temperature, add an aqueous solution of mono-sodium phosphate and then an aqueous solution of disodium phosphate. Upon reaching 69° C., add the ammonium xylenesulfonate to the mixture and heat to from about 74° C. to 77° C. add the coconut monoethanolamide, mixing until well dispersed, the ethylene glycol distearate and about 4.5% of the water. Continue mixing until homogeneous and cool mixture to about 41° C. Pump the mixture into a second tank and add the ammonium laureth sulfate, DMDM hydantoin, and aqueous solution of citric acid. In a beaker, pre-mix the natural pyrethrins and the permethrin. Add it to the second tank and q.s. to 100% with water. Mix thoroughly, cool to about 27° C., and pump the mixture into storage drums.

EXAMPLE V

A shampoo composition of the present invention is made as follows.

| Component | Weight |
|---|---|
| Ammonium Laureth Sulfate | 14.15 |
| Ammonium Lauryl Sulfate | 3.14 |
| Coconut Monoethanolamide | 3.00 |
| Ethylene Glycol Distearate | 3.00 |
| Silicone Gum[1] | 0.50 |
| Dimethicone fluid (350 cp) | 0.50 |
| Tricetyl Methyl Ammonium Chloride | 0.29 |
| Cetyl Alcohol | 0.42 |
| Stearyl Alcohol | 0.18 |
| DMDM Hydantoin | 0.20 |
| Sodium Chloride | 0.90 |
| Ammonium Chloride | 0.05 |
| Ammonium Xylenesulfonate | 1.25 |
| Natural Pyrethrins | 0.04 |
| Permethrin[2] | 0.36 |
| Water q.s. to | 100.00 |

[1] Silicone gum available from The General Electric Co. as SE-30 or SE-76 Gum.
[2] Available from McLaughlin, Gormley, and King Company.

The composition is prepared by adding approximately 0.5% of the ammonium laureth sulfate and the dimethicone to a container, and mixing for approximately 30 minutes. Add approximately 2% ammonium laureth sulfate to a processing tank and heat to between 68° C. to 71° C. Add about 0.12% stearyl alcohol, about 0.06% of cetyl alcohol, and the contents of the first container to the processing tank. Mix until uniform, maintaining the mixture between 68° C. and 71° C. Add to a second processing tank, ammonium lauryl sulfate and heat to about 71° C. While maintaining this temperature, add 0.05% ammonium chloride, about 18% water, ammonium xylenesulfonate and the remainder of the stearyl and cetyl alcohols. Add coconut monoethanolamide, tricetyl methyl ammonium chloride, ethylene glycol distearate, approximately half the DMDM hydantoin and the contents of the first tank to the second tank while maintaining a temperature of about 77° C. Mix until homogeneous and then cool to about 41° C. Pump to a third tank and add the remainder of the ammonium laureth sulfate, DMDM hydantoin, and sodium chloride. Pre-mix the permethrin and natural pyrethrins in a beaker, add it to the mixture and q.s. to 100% with water. Mix thoroughly, cool to about 27° C., and pump the mixture into storage drums.

EXAMPLE VI

A shampoo composition of the present invention is as follows.

| Component | Weight % |
|---|---|
| Ammonium Laureth Sulfate | 12.81 |
| Ammonium Lauryl Sulfate | 9.10 |
| Coconut Diethanolamide | 2.30 |
| Isostearyl Ethylmidonium Ethosulfate | 1.25 |
| DMDM Hydantoin | 0.20 |
| Monosodium phosphate | 0.50 |
| Disodium phosphate | 0.38 |
| Sodium Chloride | 0.04 |
| Citric Acid | 0.10 |
| Ammonium Xylenesulfonate | 1.35 |
| Natural Pyrethrins | 0.06 |
| Permethrin[1] | 0.50 |
| Water q.s. to | 100.00 |

[1] Available from FMC Corporation.

The composition is prepared by adding about 6.5% of the water and the ammonium laureth sulfate to a mixing tank, heating to about 35° C. While maintaining this temperature, the following components are individually added in sequence with mixing such that each component is well mixed into the batch: ammonium lauryl sulfate, ammonium xylenesulfonate, monosodium phosphate, disodium phosphate, DMDM hydantoin, sodium chloride, a solution of citric acid and water, a solution of coconut diethanolamide and isostearyl ethylmidonium ethosulfate. Pre-mix the natural pyrethrin and permethrin in a beaker, add to the mixture, and q.s. to 100% with water. Mix thoroughly, cool to about 27° C., and pump the mixture into storage drums.

All the above are storage stable shampoo compositions which clean the heat and are useful as an anti-lice treatment.

EXAMPLE VII

A conditioner composition of the present invention is as follows.

| Component | Weight % |
|---|---|
| Cetyl Alcohol | 1.00 |
| Stearyl Alcohol | 0.72 |
| DMDM Hydantoin | 0.20 |
| Hydroxyethyl Cellulose | 0.50 |
| Quaternium-18 | 0.85 |
| Ceteareth-20 | 0.35 |
| Stearalkonium Chloride | 0.85 |
| Glyceryl Monostearate | 0.25 |
| Citric Acid | 0.08 |
| Silicone Gum[1] | 0.30 |
| Cyclomethicone fluid | 1.70 |
| Natural Pyrethrins | 0.14 |
| Phenothrin[2] | 0.86 |
| Water q.s. to | 100.00 |

[1] Silicone gum available from The General Electric Company as SE-30 or SE-76 Gum.
[2] Available from Sumitomo Chemical Company as Sumithrin.

All components, except the DMDM hydantoin, citric acid, silicone gum, cyclomethicone, and pediculicide actives, are combined in a processing tank and heated to about 88° C. After the solution is thoroughly mixed, it is cooled to approximately 48° C. In a separate tank, pre-mix the silicone gum and cyclomethicone with heat and agitation to form a gum solution. The actives are thoroughly mixed in a beaker and added to the mixture above. Add the gum solution and all remaining components, q.s. with water. Mix thoroughly, cool to about 27° C., and pump the mixture into storage drums.

EXAMPLE VIII

A conditioner composition of the present invention is as follows.

| Component | Weight % |
|---|---|
| Cetyl Alcohol | 1.00 |
| Stearyl Alcohol | 0.72 |
| DMDM Hydantoin | 0.20 |
| Hydroxyethyl Cellulose | 0.50 |
| Quaterium-18 | 0.85 |
| Ceteareth-20 | 0.35 |
| Stearamidopropyldimethyl Amine (SAPDMA) | 0.50 |
| Glyceryl Monostearate | 0.25 |
| Citric Acid | 0.08 |
| Sodium Citrate | 0.05 |
| Stearoxydimethicone | 0.10 |
| Silicone Gum[1] | 0.05 |
| Cyclomethicone fluid | 1.70 |
| Natural Pyrethrins | 0.10 |
| Permethrin[2] | 0.90 |
| Water q.s. to | 100.00 |

[1]Silicone gum available from The General Electric Company as SE-30 or Se-76 Gum.
[2]Available from Mitchell Cotts Chemicals.

This conditioning anti-lice product is made in a manner similar to that described in Example VII.

All the above are storage stable conditioner compositions which condition the hair and are useful as an anti-lice treatment.

What is claimed is:

1. An ovicidal/pediculicidal hair care composition comprising:
    a) a synthetic pyrethroid selected from the group consisting of phenothrin, permethrin, and mixtures thereof;
    (b) a natural pyrethrin selected from the group consisting of esters of Cinerin I, Cinerin II, Jasmolin I, Jasmolin II, Pyrethrin I, and Pyrethrin II and mixtures thereof wherein Pyrethrin I and Pyrethrin II comprise about 70% of the said mixture; and
    (c) an acceptable liquid hair care vehicle;
wherein the ratio of (a) to (b) is from about 6:1 to about 10:1.

2. An ovicidal/pediculicidal composition according to claim 1 wherein the ratio of (a) to (b) is from about 7:1 to about 9:1.

3. An ovicidal/pediculicidal composition according to claim 2 wherein the ratio of (a) to (b) is about 9:1.

4. An ovicidal/pediculicidal hair treatment composition in the form of a shampoo comprising:
    (a) from about 0.1% to about 2.5% of the ovicidal/pediculicidal composition according to claim 1;
    (b) from about 5% to about 30% of a synthetic surfactant;
    (c) from about 1% to about 7% of an amide; and
    (d) water.

5. A shampoo form ovicidal/pediculicidal hair treatment composition according to claim 4 wherein the synthetic surfactant is selected from the group consisting of anionic, amphoteric, cationic, zwitterionic, non-ionic surfactants, and mixtures thereof.

6. A shampoo form ovicidal/pediculicidal hair treatment composition according to claim 5 wherein the amide is selected from the group consisting of coconut monoethanolamide, coconut diethanolamide and mixtures thereof.

7. A shampoo form ovicidal/pediculicidal hair treatment composition according to claim 5 additionally comprising from about 1% to about 10% of a nonvolatile silicone material.

8. A shampoo form ovicidal/pediculicidal hair treatment composition according to claim 7 wherein the non-volatile silicone is selected from the group consisting of polyalkyl siloxanes, polyalkylaryl siloxanes, polyether siloxane co-polymers, and mixtures thereof, whose viscosity is from about 100 centipoise to about 150,000,000 centipoise at 25° C.

9. A shampoo form ovicidal/pediculicidal hair treatment composition according to claim 8 additionally comprising from about 0.5% to about 5% of a suspending agent selected from the group consisting of crystalline amphiphilic materials having needle-like or platelet structures, polymeric materials, clays, fumed metal oxides, and mixtures thereof.

10. A shampoo form ovicidal/pediculicidal hair treatment composition according to claim 9 wherein the suspending agent is a crystalline amphiphilic material selected from the group consisting of long chain $C_{16}$–$C_{22}$ acyl derivatives, long chain $C_{16}$–$C_{22}$ alkanolamides of fatty acids, and mixtures thereof.

11. A shampoo form ovicidal/pediculicidal hair treatment composition according to claim 10 wherein the suspending agent is an ethylene glycol diester.

12. A shampoo form ovicidal/pediculicidal hair treatment composition according to claim 5 wherein the synthetic pyrethroid is permethrin.

13. A shampoo form ovicidal/pediculicidal hair treatment composition according to claim 5 wherein the natural Pyrethrin comprises about 70% of Pyrethrin I and Pyrethrin II esters.

14. A shampoo form ovicidal/pediculicidal hair treatment composition according to claim 5 wherein the ovicidal/pediculicidal composition has a ratio of synthetic pyrethroids to natural pyrethrins of from about 7:1 to about 9:1.

15. A shampoo form ovicidal/pediculicidal hair treatment composition according to claim 5 wherein the ovicidal/pediculicidal active is at a level from about 0.25% to about 1.5%.

16. A shampoo form ovicidal/pediculicidal hair treatment compositon according to claim 15 wherein the ovicidal/pediculicidal composition has a ratio of synthetic pyrethroids to natural pyrethrins of about 9:1.

17. A shampoo form ovicidal/pediculicidal hair treatment composition according to claim 16 wherein the ovicidal/pediculicidal active is at a level from about 0.5% to about 1%.

18. A method for treating human hair to kill and facilitate removal of lice and their eggs comprising:
    (a) applying from about 10 g to about 30 g of a composition according to claim 4 to wet hair;
    (b) working said composition through the hair and scalp;
    (c) leaving said composition on the hair and scalp for approximately 6-10 minutes;
    (d) rinsing said composition from the hair; and
    (e) repeating steps (a) to (d) until the hair is clean.

* * * * *